(12) United States Patent
Liu et al.

(10) Patent No.: US 11,686,718 B2
(45) Date of Patent: Jun. 27, 2023

(54) APPARATUS, BUFFER AND METHOD FOR PH CONTROL

(71) Applicant: University of Hertfordshire Higher Education Corporation, Hertfordshire (GB)

(72) Inventors: Fang Liu, Hertfordshire (GB); Andrew Curl, Hertfordshire (GB); Dean Fitzgerald, Hertfordshire (GB)

(73) Assignee: University of Hertfordshire Higher Education Corporation, Hertfordshire (GB)

( * ) Notice: Subject to any disclaimer, the term of this patent is extended or adjusted under 35 U.S.C. 154(b) by 507 days.

(21) Appl. No.: 16/647,136

(22) PCT Filed: Sep. 14, 2018

(86) PCT No.: PCT/GB2018/052625
§ 371 (c)(1),
(2) Date: Mar. 13, 2020

(87) PCT Pub. No.: WO2019/053451
PCT Pub. Date: Mar. 21, 2019

(65) Prior Publication Data
US 2021/0033588 A1 Feb. 4, 2021

(30) Foreign Application Priority Data
Sep. 16, 2017 (GB) .................... 1714942

(51) Int. Cl.
*G01N 33/15* (2006.01)
*G01N 13/00* (2006.01)
(Continued)

(52) U.S. Cl.
CPC ....... *G01N 33/15* (2013.01); *B01F 23/23121* (2022.01); *G01N 13/00* (2013.01);
(Continued)

(58) Field of Classification Search
CPC ........ B01F 23/23121; B01F 23/231231; B01F 23/231266; B01F 23/231267;
(Continued)

(56) References Cited

U.S. PATENT DOCUMENTS 3,707,067 A * 12/1972 Dietrick ................ B01D 47/06
261/78.2
3,791,222 A 2/1974 Goodhart et al.
(Continued)

FOREIGN PATENT DOCUMENTS

| CN | 201827888 U | 5/2011 |
| CN | 203177172 U | 9/2013 |

(Continued)

OTHER PUBLICATIONS

Liu F et al., "A novel concept in enteric coating: a double-coating system providing rapid drug release in the proximal small intestine", Journal of Controlled Release, Elsevier, Amsterdam, NL, vol. 133, No. 2, Jan. 19, 2009, pp. 119-124.
(Continued)

*Primary Examiner* — Charles S Bushey
(74) *Attorney, Agent, or Firm* — Wood Herron & Evans LLP

(57) ABSTRACT

An apparatus, buffer solutions and a method are provided for pH control of in vitro dissolution tests used to monitor the drug release rate from solid unit dosage forms which are used to predict their in vivo effects or for quality control purposes. A method of preparing a continuous condition and a clear bicarbonate ion based solution for in vitro dissolution testing of pharmaceutical products is also provided.
An enclosure device is also provided for use in the provision of pH control and stabilization to a bicarbonate based solution used in the in vitro dissolution testing of pharmaceutical products.

14 Claims, 12 Drawing Sheets

(51) Int. Cl.
  *B01F 23/231* (2022.01)
  *B01F 23/237* (2022.01)
  *B01F 101/23* (2022.01)
(52) U.S. Cl.
  CPC . *B01F 23/23762* (2022.01); *B01F 23/231231* (2022.01); *B01F 23/231262* (2022.01); *B01F 23/237611* (2022.01); *B01F 23/237612* (2022.01); *B01F 2101/23* (2022.01); *B01F 2215/0422* (2013.01); *B01F 2215/0431* (2013.01); *B01F 2215/0468* (2013.01); *G01N 2013/006* (2013.01)
(58) Field of Classification Search
  CPC ........ B01F 23/23762; B01F 23/237612; B01F 23/237611; B01F 23/231262; B01F 2101/23; B01F 2215/0422; B01F 2215/0431; B01F 2215/0468; G01N 33/15; G01N 13/00; G01N 2013/006
  USPC .......................................................... 261/76
  See application file for complete search history.

(56) References Cited

U.S. PATENT DOCUMENTS

| | | | | |
|---|---|---|---|---|
| 4,487,553 | A * | 12/1984 | Nagata | F04F 5/466 417/171 |
| 5,807,115 | A | 9/1998 | Hu | |
| 6,461,500 | B1 * | 10/2002 | Hoage | B01F 23/2331 210/150 |
| 7,357,046 | B2 * | 4/2008 | Kraft | B01F 21/15 73/866 |
| 7,913,984 | B2 * | 3/2011 | Noguchi | B01F 25/50 261/36.1 |
| 2007/0196929 | A1 | 8/2007 | Stuart et al. | |
| 2012/0034704 | A1 | 2/2012 | Hughes et al. | |
| 2016/0325241 | A1 * | 11/2016 | May | B01F 23/23121 |

FOREIGN PATENT DOCUMENTS

| | | |
|---|---|---|
| EP | 1308710 A2 | 5/2003 |
| EP | 2402748 A1 | 1/2012 |
| WO | 2007054342 A1 | 5/2007 |
| WO | 2013164629 A1 | 11/2013 |
| WO | 2015142178 A1 | 9/2015 |

OTHER PUBLICATIONS

Heigoldt U et al.., "Predicting in vivo absorption behavior of oral modified release dosage forms containing pH-dependent poorly soluble drugs using a novel pH-adjusted biphasic in vitro dissolution test", European Journal of Pharmaceutics and Biopharmaceutics, Elsevier Science Publishers B.V., Amsterdam, NL, vol. 76, No. 1, Sep. 2010, pp. 105-111.

Fang Liu et al., "Evolution of a physiological pH6.8 biocarbonate buffer system: Application to the dissolution testing of enteric coated products", European Journal of Pharmaceutics and Biopharmaceutics, Elsevier Science Publishers B.V., Amsterdam, NL, vol. 78, No. 1, Jan. 11, 2011, pp. 151-157.

Intellectual Property Office of the United Kingdom, Patents Act 1977: Combined Search and Examination Report under Sections 17 and 18(3), Application No. GB1714942.8, dated Jun. 26, 2018 (5 pages).

European Patent Office, International Search Report and Written Opinion of the International Searching Authority, International Application No. PCT/GB2018/052625, dated Mar. 27, 2019 (19 pages).

Intellectual Property Office of the United Kingdom, Patents Act 1977: Search Report under Section 17(6), Application No. GB1714942. 8, dated Oct. 8, 2019 (5 pages).

European Patent Office, Examination Report, Application No. 18773579. 0, dated Jul. 14, 2022 (5 pages).

* cited by examiner

# APPARATUS, BUFFER AND METHOD FOR PH CONTROL

CROSS-REFERENCE TO RELATED APPLICATIONS

This application is a submission under 35 U.S.C. § 371 of International Application No. PCT/GB2018/052625, filed Sep. 14, 2018, which claims priority to Great Britain Application No. 1714942.8, filed Sep. 16, 2017, the disclosures of which are hereby expressly incorporated by reference herein in their entireties.

FIELD OF THE INVENTION

The present invention relates to an apparatus, buffer solutions and a method for pH control of in vitro dissolution tests used to monitor the drug release rate from solid unit dosage forms which are used to predict their in vivo effects or for quality control purposes.

BACKGROUND

Medications that are intended to be taken orally are commonly made into solid units (dosage forms/formulations) such as tablets, capsules, granules and pellets. When these solid units reach the gastrointestinal tract, they often disintegrate and release the active drug content into the gastrointestinal fluid to be absorbed into the systemic circulation. The rate at which the active drug is released from the solid dosage form can determine how quickly the drug is absorbed and start its therapeutic effect. This rate is dependent on many factors including the physiochemical properties of the drug (e.g. solubility and particle size), the formulation that carries the drug and the physiological conditions of the gastrointestinal tract (e.g. gastric emptying time, pH, buffer capacity and fluid volume). The formulations that carry active drugs can be divided into two major types; the first type provides immediate drug release where the drug is typically released from the solid unit and dissolves in the stomach fluid and the second type modifies the drug release rate. The second type can be pH-dependent depositing the drug in a particular region of the gastrointestinal tract or pH-independent providing controlled, sustained, extended, or slow drug release throughout the gut.

In vitro dissolution tests are used to monitor the drug release rate from such solid unit dosage forms to predict their in vivo effects or for quality control purposes. Different in vitro models and apparatus are used to determine drug release rates from solid unit dosage forms and include the Dynamic Gastric Model and the TNO gastro-intestinal model (TIM). However, the most common tests use simplified apparatus as set out in the United States Pharmacopeia (USP) specifications, namely USP-I (rotating basket), USP-II (paddle), USP-III (reciprocating cylinder) and USP-IV (flow-through) apparatus.

The types of media that are used in the dissolution apparatus have an impact on the drug release rate obtained. The most commonly used dissolution media includes water, 0.1 M HCl and simple phosphate based buffer solution. To better simulate the conditions of the gastrointestinal fluid, biorelevant media are used such as Simulated Gastric Fluid (SGF) and Simulated Intestinal Fluid (SIF). These types of media can mimic the conditions of the fasted and fed state of the stomach and intestine and as such they can take into account the pH, buffer capacity, osmolality, surface tension, lipid and bile salt content of the gastrointestinal tract.

Another aspect of the dissolution media is the buffer species used. Research has shown that different buffer species in the dissolution media can have an impact on the drug release rate, in particular for ionisable drugs (which are either weakly acidic or weakly basic) and drug releases from formulations that have a pH-dependent coating applied to them. The principle buffer species in the human intestinal fluid is bicarbonate which is secreted from epithelial cells and glands to neutralize acidic gastric juices. However, in such in vitro testing phosphate buffers tend to be most commonly used as the dissolution media. Even in the above mentioned biorelevant media, the buffer species used tend to be acetic or maleic acid based.

The key to a buffer system for in vitro dissolution testing is to mimic the physiological conditions of the gastrointestinal fluid with the right balance of ionic composition. J Hanks created a balanced salt solution (Hanks solution) which simulates the inorganic salt composition of mammalian cells. Hanks solution is primarily buffered with bicarbonate to give the pH control. Another similar physiological solution is the Krebs-Henseleit (KH) Buffer which contains a higher bicarbonate concentration and a higher buffer capacity. When such physiological bicarbonate buffers are used for in vitro dissolution testing though they cannot control a stabilised pH, this is due to the loss of carbon dioxide to the atmosphere which increases the pH of the solution. One method used to provide this pH stabilisation for dissolution testing is the complete sealing of the apparatus system and applying an oil layer on top of the media solution. WO 2013/164629 (Merchant et al) sets out another method of alternately purging $CO_2$ and an inert gas into the solution to control the pH. However, purging gases directly into the dissolution media changes hydrodynamics of the test conditions and creates foaming when the media is mixed with lipids and bile salts which are used to create a biorelevant media.

When testing the drug release from solid units that are surrounded by a pH-dependent coating, a two-stage approach is usually required; the first stage simulates the stomach pH (pH 1-2), commonly using 0.1 M HCl and the second stage mimics the intestinal pH conditions (pH 6-8). Such two-stage tests can also be adapted for testing ionisable compounds in controlled release formulations. When physiological bicarbonate solutions are used for in vitro dissolution testing, however, they require a complete disposal of the media that is used for the first stage testing and the test samples need to be transferred to a second media containing the bicarbonate salt for the second stage testing. This is labour intensive, time consuming and impractical in particular when testing the drug release from solid units in a multi-particulate form such as pellets, granules, microparticles, microspheres and micropellets that are often beneficial for children and older patients.

SUMMARY OF THE INVENTION

According to the first aspect of the present invention there is provided a method of preparing physiological bicarbonate solutions for in vitro dissolution testing of pharmaceutical products such that a phase transfer is not required. The test is conducted in two stages (e.g. an acid stage and a buffer stage) whilst the product remains in a single compartment or vessel. The acidic solution used in the acid stage is typically an aqueous solution of hydrochloric acid which is neutralised to a near neutral or a slightly basic pH to create the second (buffer) stage. The buffer stage utilises bicarbonate as the main buffering species for pH control and mimics the conditions of the human intestinal fluid in terms of the balanced ionic composition and the content of lipids and bile salts. The method used in this invention prevents the precipitation of certain salts during the transition from the acidic solution to the buffer solution which often occurs during the production of the balanced salt solution to simulate the ionic composition of the intestinal fluid. It also minimises the loss of the bicarbonate species in the aqueous solution prior to the commencement of the dissolution testing.

The first aspect of the invention involves the creation of a continuous condition and a clear bicarbonate ion based solution for in vitro dissolution testing of pharmaceutical products. The test is conducted in two stages (e.g. an acid stage and a buffer stage) while the product remains in a single compartment or vessel. In one aspect of the invention, an acidic solution (solution A) typically made of aqueous solutions of hydrochloric acid (as known in the area of art) is held in a compartment or container typically made of glass or other non-reactive material. The pH of such an acidic solution is preferably in the range of 0.5-4.5 which is dependent on the concentration of the acid. Preferably, the pH is in the range of 1-3 and most preferably 1-2. Solution A preferably simulates the in vivo conditions of human stomach both in the fasted state and the fed state in terms of ionic composition and lipid content.

After exposure of the solid unit of the test pharmaceutical product in solution A for a pre-determined time period, various other solutions are then added to solution A to change the test condition to mimic the in vivo conditions of the small intestine in terms of ionic composition and lipid content. These solutions include:

Solution B: An alkaline solution containing a certain concentration of a base which accepts protons from any proton donor and/or completely or partially releases hydroxide ions in an aqueous environment. Solution B is preferably made by dissolving sodium hydroxide and other hydroxides of the alkali metals and alkaline earth metals including lithium, potassium, magnesium and calcium in water.

Solution C: A solution containing inorganic salts dissolved in water which completely or partially dissociate into ions of phosphate, potassium, sodium, chloride, calcium and magnesium. Examples of suitable inorganic salts include sodium chloride, potassium chloride, magnesium sulfate, calcium chloride, sodium phosphate dibasic, potassium dihydrogen orthophosphate, sodium phosphate tribasic and sodium dihydrate phosphate.

Solution D: A solution containing bicarbonate ions in aqueous solution. Solution D is preferably made by dissolving salts of carbonic acid in water. Examples of suitable salts include lithium carbonate, lithium hydrogen carbonate, sodium carbonate, sodium hydrogen carbonate (sodium bicarbonate), trisodium hydrogendicarbonate, potassium carbonate, potassium hydrogen carbonate (potassium bicarbonate), magnesium carbonate, magnesium hydrogen carbonate (magnesium bicarbonate), calcium carbonate, calcium hydrogen carbonate (calcium bicarbonate), iron carbonate, aluminium carbonate, ammonium carbonate, ammonium bicarbonate.

Solution E: A solution containing lipids and bile salts that can typically be found in the human gastrointestinal fluids. Examples of suitable lipids and bile salts include lecithins, phospholipids, cholic acid and its salts, glycocholic acid and its salts, taurocholic acid and its salts, deoxycholic acid and its salts, chenodeoxycholic acid and its salts, glycochenodeoxycholic acid and its salts, taurochenodeoxycholic acid and its salts, and lithocholic acid and its salts.

In one alternative, solution B is added into solution A before the other solutions are introduced.

In another alternative, solutions C and D are mixed together prior adding into solution A. Preferably, the said bicarbonate or carbonate salts used in solution D are added into solution C as a powder and dissolved just before the solution is added to solution A.

In another alternative, solutions C, D and E are mixed together prior adding into solution A. Preferably, the lipids and bile salts of solution E are added to solution C as a powder and dissolved (mixture of solutions C and E) then the said bicarbonate or carbonate salts used in solution D are added into this mixture of solution C and E as a powder and dissolved just before the final mixed solution is added to solution A. In an alternative, only solutions B, C and D are added into solution A.

The resulting solution (solution F) obtained from adding the various solution combinations set out above to solution A simulates the ionic and lipid conditions of the human intestinal fluid. The pH of solution F is preferably in the range of 5-8 which reflects the inter- and intra-individual variations in human intestine and the gradual changes in intestinal pH from the proximal intestinal (duodenum) to the distal intestine (ileum) and further to the large intestine (colon).

According to a second aspect of the present invention there is provided an apparatus which is used to pH stabilise the bicarbonate-based media which will not create bubbles in the solution and as such is compatible with lipids and bile salts for biorelevant testing.

The second aspect of the invention involves an apparatus which can provide pH control and stabilisation to a bicarbonate based solution for use in the in vitro dissolution testing of pharmaceutical products. The bicarbonate based solution can be solution F as described above or any other preferably freshly prepared solution containing bicarbonate ions as the primary or partial buffer specie with or without the addition of lipids and/or bile salts as would be found in a bio-relevant dissolution media. The apparatus comprises a compartment, container or vessel which is configured to contain the bicarbonate solution. The compartment is configured to be enclosed with an enclosure device that partially isolates the gas environment in the compartment with the surrounding atmosphere, however, still allowing leakage of gas into the atmosphere when the gas pressure within the container is higher than the atmosphere pressure.

In one aspect of the invention, the above said enclosure device comprises a plate attached to a ring-shaped chamber which is completely or partially hollow inside. The plate contains at least one aperture and preferably two or more apertures that extend through the entire thickness of the plate. Each aperture is configured to be connected to a supply of gas at one end thereof, preferably this is achieved by connecting a tube preferably made of metal (e.g. stainless steel or copper) or other suitable materials as known in the art into each of the apertures provided. Preferably the diameter of each of the tubes is 1-10 mm and preferably 1-5 mm. The tube is connected to the supply of a gas which, when dissolved into the bicarbonate solution, will increase or decrease the pH. In an alternative where a single aperture is provided a t-junction may be provided which splits. The other end of the apertures connect either directly or through a channel into the hollow cavity in the ring-shaped chamber. At the bottom of the ring-shaped chamber (opposite to the plate), a plurality of orifices are made through the entire depth thereof. The distance between each of the orifices is in the range of 1-150 mm and preferably 1-50 mm and most preferably 5-20 mm. The diameter of each of the orifices is 0.1-2 mm and preferably 0.5-1.5 mm. The angle at which each of the orifices passes through the bottom of the ring-shaped chamber is in the range of 45-90° in reference to the surface of the liquid (dissolution media) in the dissolution compartment. The orifices can be unidirectional (such as all in 90° angle in reference to the surface of the liquid) or in multiple-directions with mixed angles from 45-90° in reference to the surface of the liquid.

Preferably the above mentioned ring-shaped chamber is in the shape of a circle or an oval. The diameter of a circular shape or the length of the longest side of an oval shape is preferably 50-150 mm, more preferably 50-135 mm and most preferably 80-120 mm. The length of the shortest side of an oval shape is preferably 20-100 mm and more preferably 30-80 mm. The height of the ring-shaped chamber is the distance between the bottom of the chamber to the maximum height of the liquid in the dissolution compartment. Such distance is in the range of preferably 1-50 mm and more preferably 5-20 mm. In one aspect of the invention, the chamber is attached to the base plate and the chamber is completely hollow inside. The gas is supplied through the aperture on the base plate directly into the hollowed cavity in the chamber. In another aspect of the invention, the chamber is attached to the base plate and the chamber is partially hollow inside. The gas is supplied through the aperture on the base plate through a channel into the hollowed cavity in the chamber. The diameter of the hollowed cavity in the chamber is in the range of preferably 1-50 mm and more preferably 5-20 mm.

In another aspect of the invention, the above mentioned ring-shaped chamber is attached to the base plate at 2-3 points where the apertures on the base plate locate. The connections are made through vertical tubes (at 90° angle to the base plate) of diameters of preferably 1-10 mm and more preferably 1-5 mm. In this aspect of the invention, the chamber is completely hollow inside and connected via the vertical tubes to the base plate. The gas is supplied through the aperture on the base plate and then passes through each of the vertical tubes to reach the hollowed cavity in the chamber. The diameter of the ring-shaped chamber in this aspect is in the range of preferably 1-50 mm and more preferably 5-20 mm.

Preferably the material of the base plate and the chamber is acrylic glass or any other inert and non-reactive material as known in the art. The base plate and the above said chamber are connected by heat-shrink techniques known to the art, for example through a spigot which connects to the base plate through a lip and which is designed to fit tightly to the chamber. In another aspect of the invention, the base plate and the chamber are manufactured as a single unit avoid the need of the spigot and the lid, such manufacture as a single unit may for example be through the use of 3D printing techniques.

According to a third aspect of the present invention there is provided a method which is used to pH stabilise the bicarbonate-based media which will not create bubbles in the solution and as such is compatible with lipids and bile salts for biorelevant testing.

The third aspect of the invention involves an apparatus described above which can provide pH control and stabilisation to a bicarbonate based solution for use in the in vitro dissolution testing of pharmaceutical products. The bicarbonate based solution can be solution F as described above or any other preferably freshly prepared solution containing bicarbonate ions as the primary or partial buffer specie with or without the addition of lipids and/or bile salts as would be found in a bio-relevant dissolution media. The apparatus as described above comprises a compartment, container or vessel which contains the bicarbonate solution. The compartment is enclosed with an enclosure device as described above that partially isolates the gas environment in the compartment with the surrounding atmosphere, however, still allowing leakage of gas into the atmosphere when the gas pressure within the container is higher than the atmosphere pressure.

The pH-decreasing gas as mentioned above is pure carbon dioxide or carbon dioxide mixed with another gas with examples as oxygen and compressed air. The concentration of carbon dioxide in the mixture is in the range of preferably 1-99% and higher than that of the earth atmosphere, which is currently 0.04%. The gas is supplied through the aperture on the base plate of the above described enclosure device, through the hollowed cavity of the ring-shaped chamber and released out through the plurality of orifices at the bottom of the ring-shaped chamber. The volume and/or pressure of the gas supply can be monitored using a gas regulator or a flow meter as known in the art. The range of the supplied carbon dioxide pressure (which could either be the pressure of the pure carbon dioxide gas or the pressure of the carbon dioxide in the gas mixture) is preferably 0.01-10 bar (1-1000 kpa), more preferably 0.05-2 bar (5-200 kpa) and most preferably 0.1-1 bar (10-100 kpa). When the partial pressure of carbon dioxide on the surface of the bicarbonate-based dissolution liquid is increased by the gas supply, more carbon dioxide will be dissolved in the liquid, and thus a higher concentration of carbonic acid is generated and further dissociated into bicarbonate and hydrogen ions. This decreases the pH of the solution. It is to be noted that, the higher the concentration of carbon dioxide in the gas mixture, the greater the effectiveness of the pH reduction in the bicarbonate-based dissolution solution. The pH-increasing gas as mentioned above is an inert gas and examples include argon, nitrogen and helium. The gas is supplied through the aperture on the base plate of the above described enclosure device, through the hollowed cavity of the ring-shaped chamber and released out through the plurality of orifices at the bottom of the ring-shaped chamber. The volume and/or pressure of the gas supply can be monitored using a gas regulator or a flow meter as known in the art. The range of the supplied gas pressure is preferably 0.1-10 bar (10-1000 kpa), more preferably 0.5-5 bar (5-500 kpa) and most preferably 2-4 bar (200-400 kpa). When the inert gas is supplied into the headspace above the bicarbonate-based dissolution media, it reduces the partial pressure of carbon dioxide on the surface of the media and the dissolved carbon dioxide will escape from the solution leading to an increase in pH. It is to be noted that the increase in the pH of the solution using the inert gas is less effective than the decrease in pH using carbon dioxide (density 1.80 kg/m3). To this end gases with higher density (e.g. argon—density 1.78 kg/m3 and nitrogen—density 1.14 kg/m3) are preferred than those with lower density (helium—density 0.16 kg/m3).

The supply of the pH-increasing and decreasing gases can be used to control the pH level of the bicarbonate-based dissolution media to stabilise it at a pre-determined pH or to increase or decrease the pH level simulating the pH changes along the intestinal tract. In one aspect of the invention, the pH of the solution is stabilised at pH 6.8 or any other pre-determined pH to simulate the average pH level of the entire intestine or the pH level of any particular region of the intestine. This type of test would usually be used for dissolution testing of gastric-resistant or enteric coated products, or any pharmaceutical products that are designed to release the active drug in a particular region of the intestine. During dissolution testing, the pH level of the bicarbonate-based media typically increases due to the loss of carbon dioxide from the solution. A supply of carbon dioxide gas through the above described enclosure device will decrease the pH to the desired level. The inert gas (e.g. argon, nitrogen or helium) can be supplied to counter any excess pH reduction if necessary. In another aspect of the invention, the pH of the solution is increased or decreased simulating the pH changes along the intestine. Typically a human intestinal pH level starts at pH 5.0-6.0 (duodenum), increases to pH 6.0-7.0 (jejunum) and then to 6.5-7.5 (ileum). There is a fall in pH level at the ileocecal junction to around 6.0-7.0 and it increases again along the colon to pH 7.0-8.0. It is to be noted that this pH profile varies significantly inter- and intra-subject and depends on many characteristics of a person such as age, gender, body weight and diet. The pH change could be achieved manually or automatically using a pH-controller and electric valves. At pre-determined time intervals when an increase in pH is required, a supply of the inert gas is provided and vice versa for the supply of carbon dioxide gas when a reduction in pH is required. The pH level of the dissolution media is measured using a pH electrode inserted into the solution as known in the art. The supply of the gas to reach the desired pH level is performed manually by opening and closing the gas regulator, or alternatively automatically using electrical solenoid valves. In the latter aspect, the opening and closing the valves is controlled by the signals from a pH control device which receives electric signals from a pH electrode inserted into the dissolution medium.

The dimension of the above described base plate of the enclosure device depends on the type and size of the compartment or vessel that holds the bicarbonate solution. This means that the dimensions of the plate need to match that of the compartment or vessel. Such a compartment or vessel can be adapted from those that are used in apparatus according to United States Pharmacopeia (USP) for dissolution testing of dosage forms, namely USP-I (rotating basket), USP-II (paddle), USP-III (reciprocating cylinder) and USP-IV (flow-through) apparatus. In addition to the apertures on the base plate that are used for supplying the gas, other openings/gaps/holes can be made in the plate. These include form example, an opening in the centre of the plate for passing through the paddle/basket holder according to the USP apparatus, an opening/hole for inserting the pH electrode into the dissolution medium, and openings for taking/returning test samples from the dissolution medium.

The above described buffer and its pH-control device and method are intended for dissolution testing of pharmaceutical products that are expected to have a therapeutic effect when ingested into the body. Such tests can be used where the product specification is already known such as in quality control during manufacturing or storage and also for predicting in vivo performance of the product known as providing in vitro in vivo correlation. The advantage of the present invention is to provide a dissolution system simulating the in vivo conditions of the gastrointestinal tract. An additional advantage is to avoid physically transferring the product or dosage form from one test condition to the next, typically from an acidic condition simulating the stomach to a neutral or alkaline condition simulating the intestine. A further advantage of the present invention is to offer pH control of the dissolution medium without causing turbulence to the solution which is said to impact the dissolution rate of the active drug from the product. Also a further advantage of the present invention is to provide pH control of the bicarbonate-based dissolution media which is compatible with lipids and bile salts which naturally occur in the gastrointestinal tract. This is achieved by avoiding bubbling/foaming which would otherwise occur when gases are purged directly into the dissolution media.

The pharmaceutical products that can be expected to benefit from dissolution testing using the above described buffer and its pH-control device and method can be in any form that is intended for oral ingestion and which provides a therapeutic effect once absorbed into the systemic circulation or for localised effects. Examples of such dosage forms include but are not limited to tablets, capsules (both hard and soft types), granules (including micro-granules and extradites), pellets (including micro-pellets), powder (including microparticles), suspensions, emulsions, films and wafers. These pharmaceutical products are expected to release the active ingredients into the gastrointestinal tract after ingestion, either immediately into the stomach, or deferred to release in any segments of the intestine, or in a controlled manner throughout the gastrointestinal tract. Such dosage forms can be further provided with an additional coating which may be applied to either mask the bitter taste, optimise stability or modify drug release. One such coating which is used to modify drug release utilises coating materials that provide pH-dependent dissolution. Such coatings typically exhibit limited dissolution in the acidic pH of the stomach and dissolve at the near neutral or slight basic pH conditions of the intestine (including any segment of the intestinal region, e.g. the proximal, middle, and distal small intestine or the colon). The dosage form can also be in the form of a controlled release device which may contain the active ingredient which is surrounded by a membrane coating or where the active ingredient is imbedded in a polymeric matrix. It is to be understood that the above mentioned are examples of the pharmaceutical product types that can be tested using the buffer and its pH-control described in this invention. The invention and its method can be applied to pharmaceutical products of any form.

BRIEF DESCRIPTION OF THE DRAWINGS

Other aspects and features of the present invention will become apparent to those ordinarily skilled in the art upon review of the following description of specific embodiments of the invention in conjunction with the accompanying figures.

DETAILED DESCRIPTION OF PREFERRED EMBODIMENTS

Figure 1:
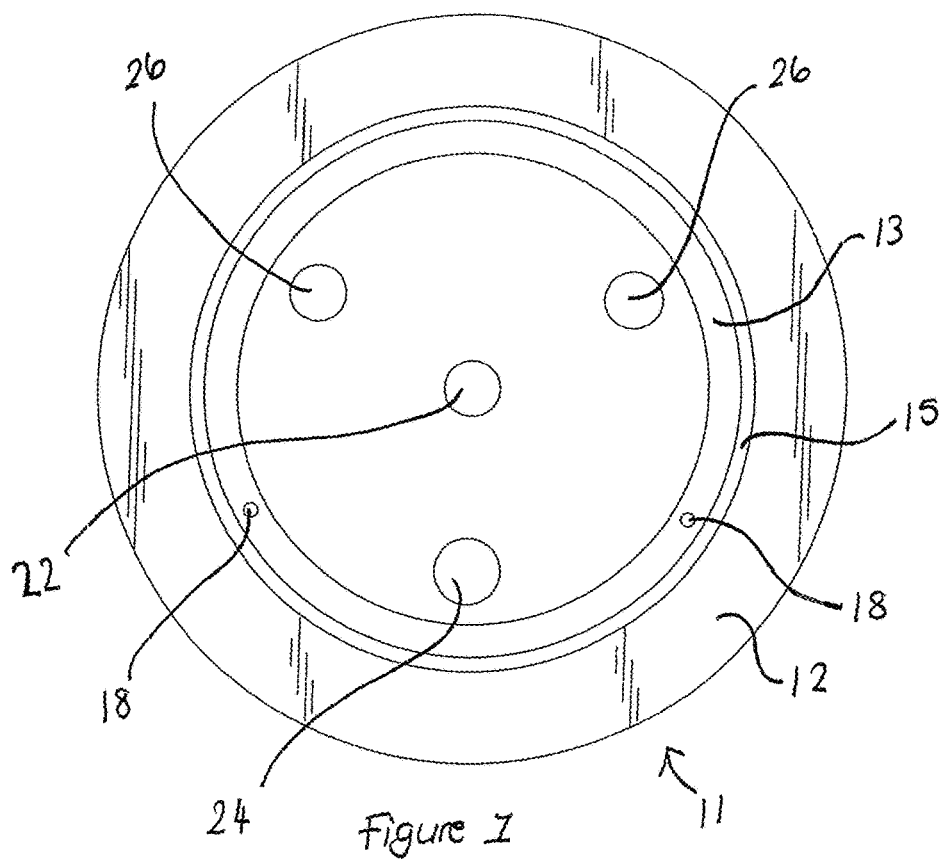
FIG. 1 illustrates a bottom plan view of the lid portion of the enclosure device.
Figure 2:
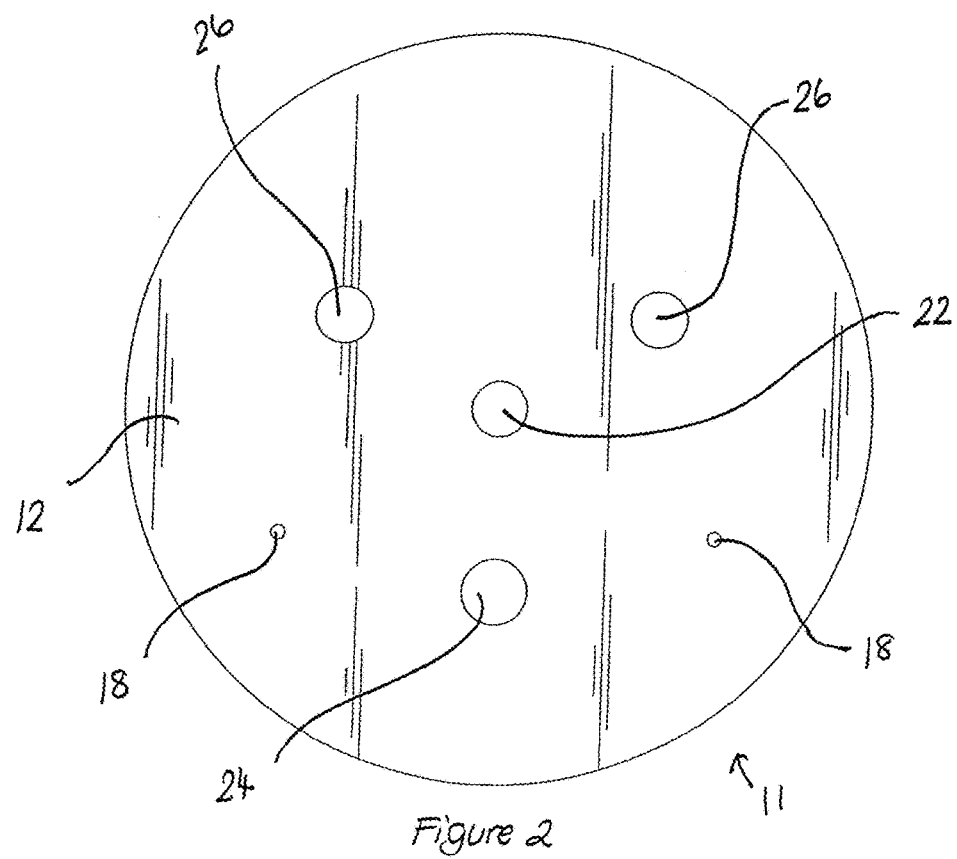
FIG. 2 illustrates a top plan view of the lid portion of the enclosure device.
Figure 3:
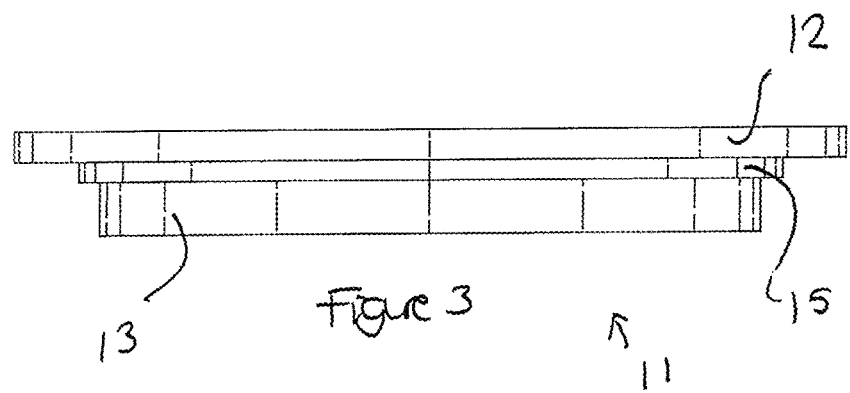
FIG. 3 illustrates a side plan view of the lid portion enclosure device.
Figure 4:
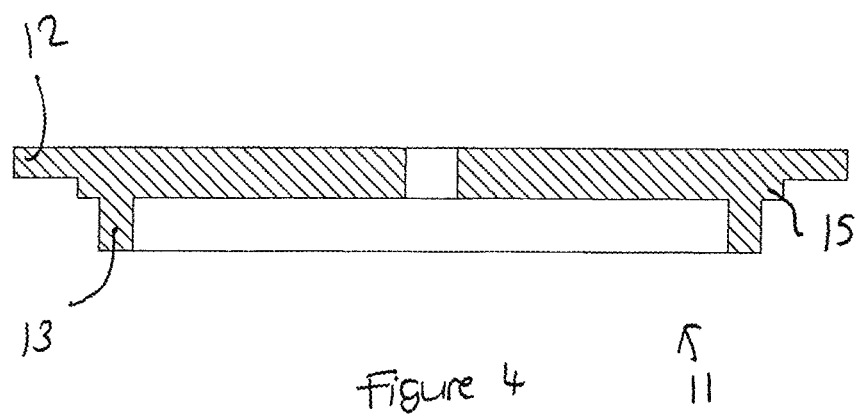
FIG. 4 illustrates a side cross-sectional view of the lid portion enclosure device.
Figure 5:
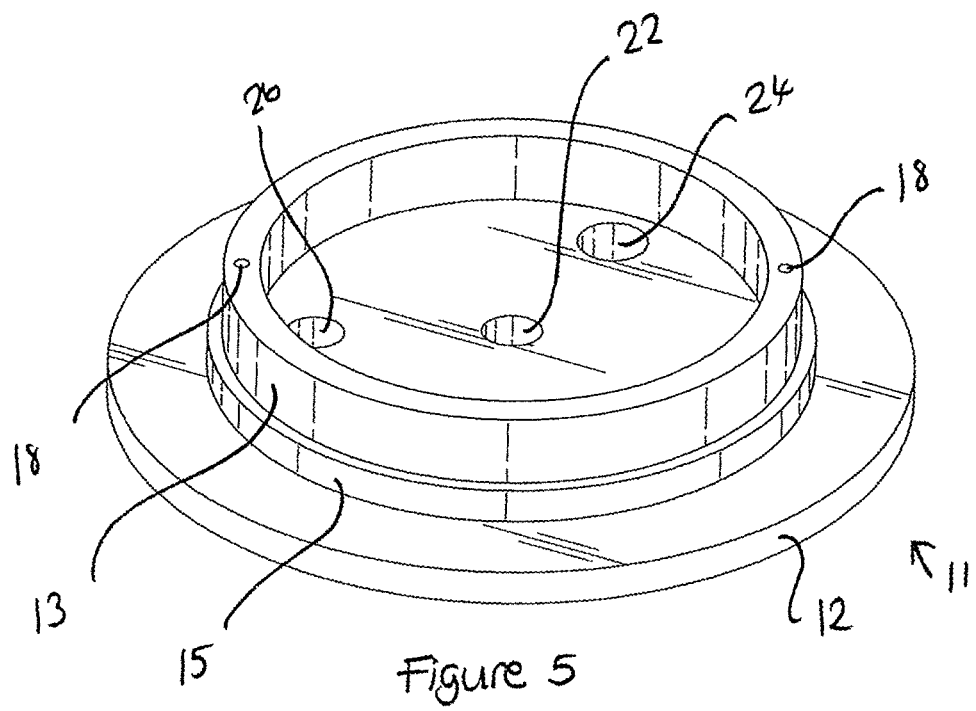
FIG. 5 illustrates a bottom perspective view of the lid portion of the enclosure device.
Figure 6:
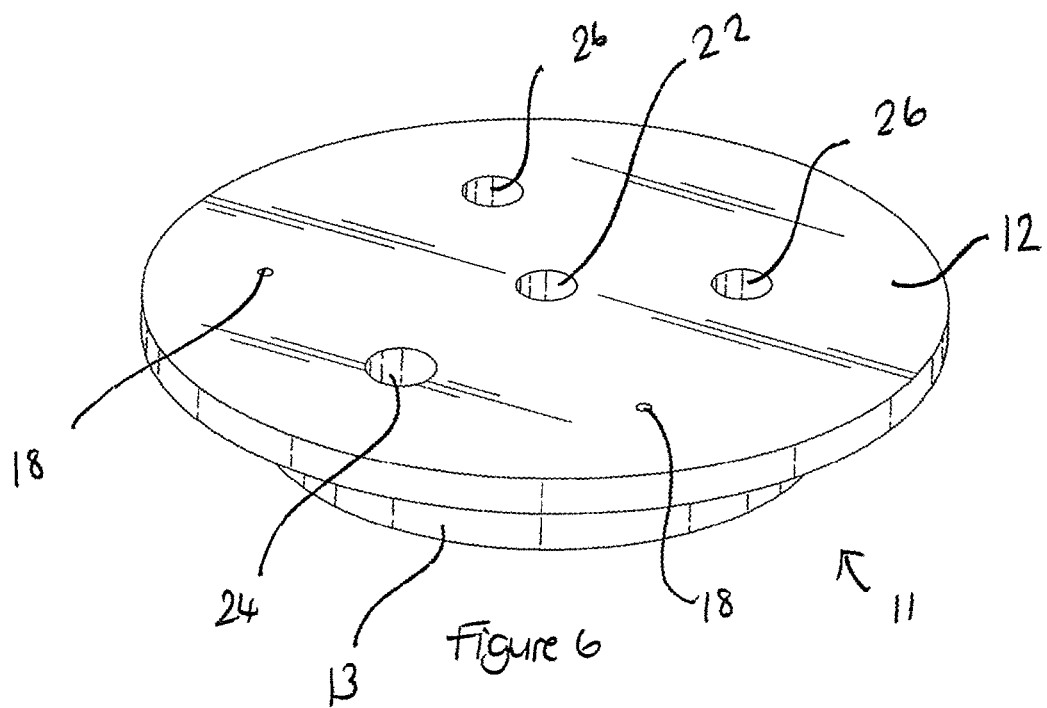
FIG. 6 illustrates a top perspective view of the lid portion of the enclosure device.
Figure 7:
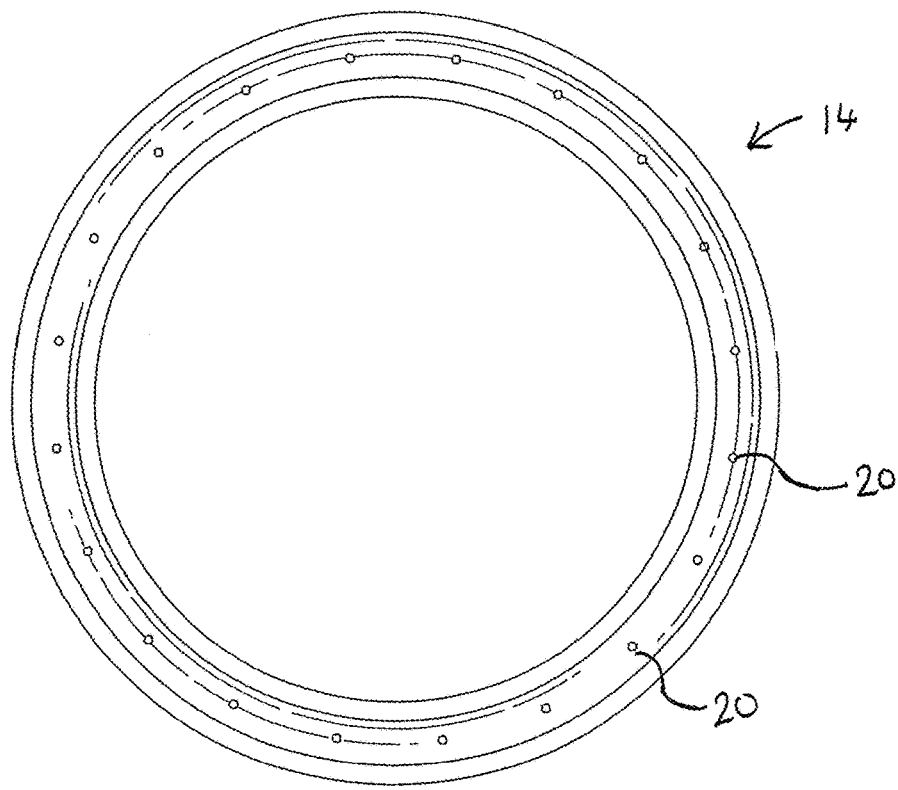
FIG. 7 illustrates a top plan view of the ring-shaped chamber of the enclosure device.
Figure 8:
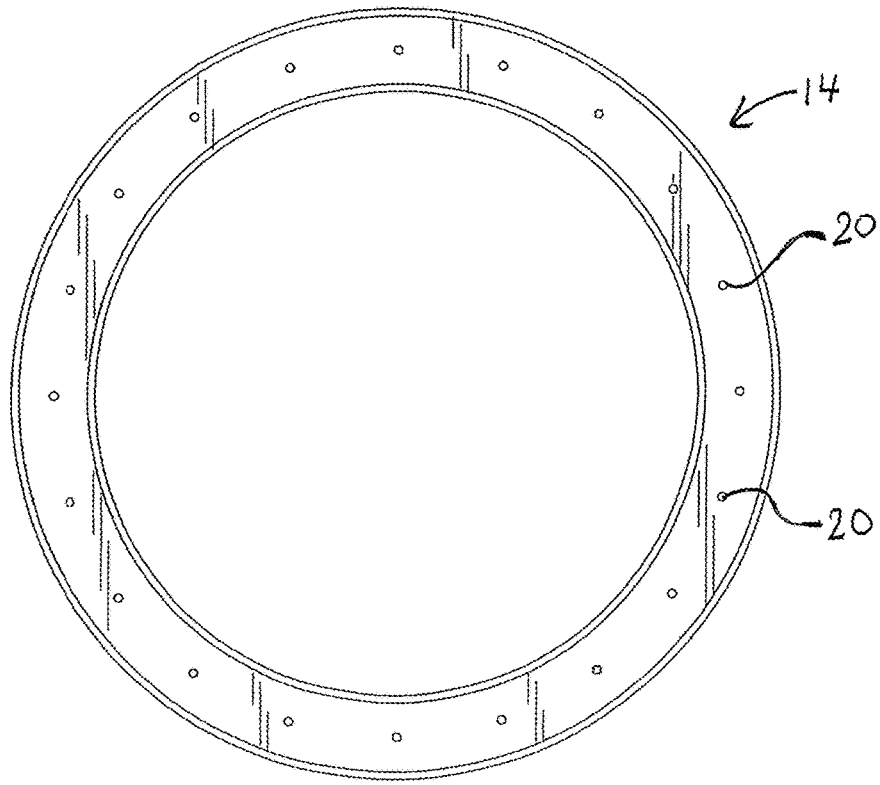
FIG. 8 illustrates a bottom plan view of the ring-shaped chamber of the enclosure device.
Figure 9:
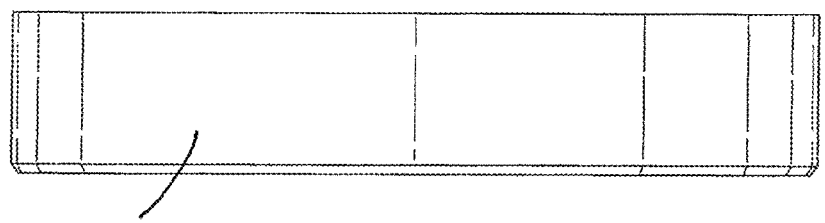
FIG. 9 illustrates a side plan view of the ring-shaped chamber of the enclosure device.
Figure 10:
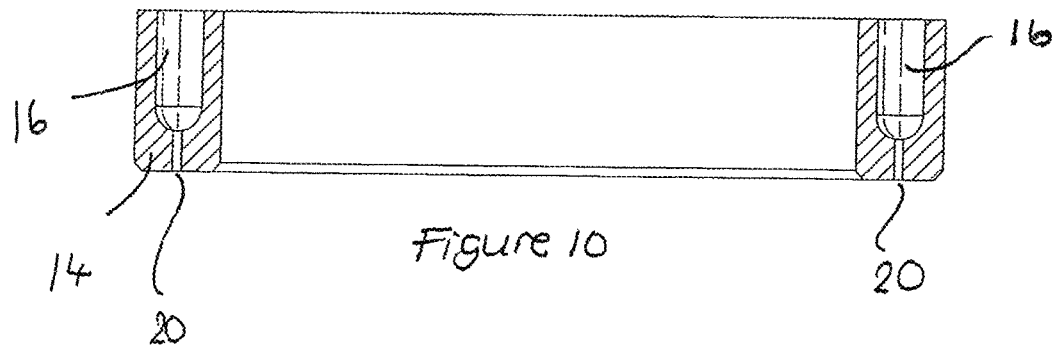
FIG. 10 illustrates a side cross-sectional view of the ring-shaped chamber of the enclosure device.
Figure 11:
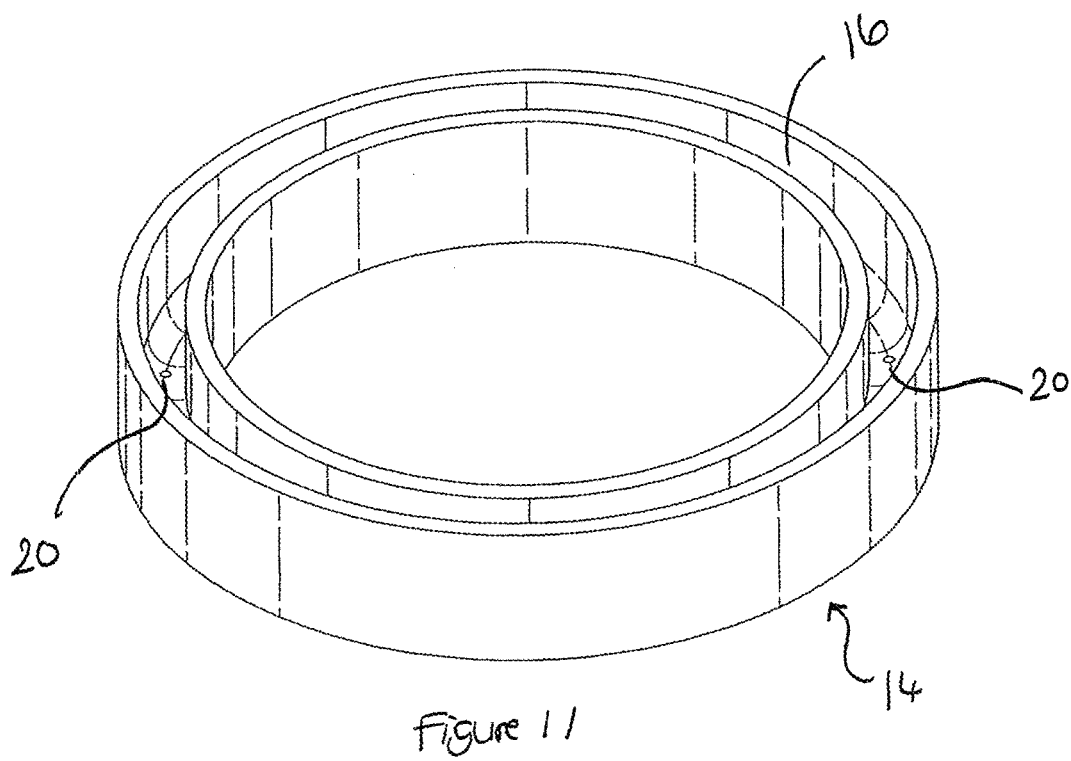
FIG. 11 illustrates a top perspective view of the ring-shaped chamber of the enclosure device.
Figure 12:
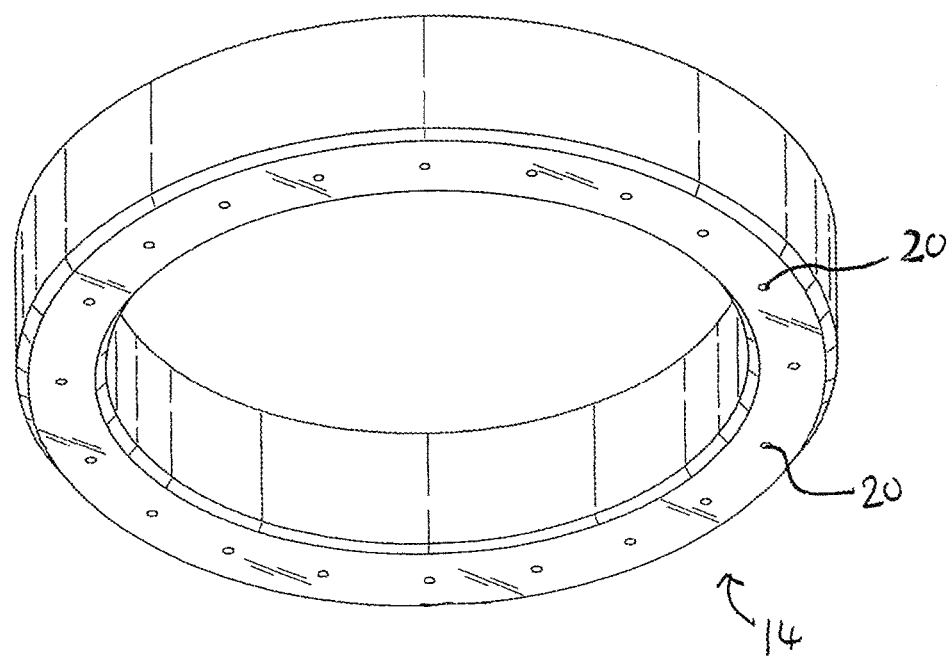
FIG. 12 illustrates a bottom perspective view of the ring-shaped chamber of the enclosure device.
Figure 13:
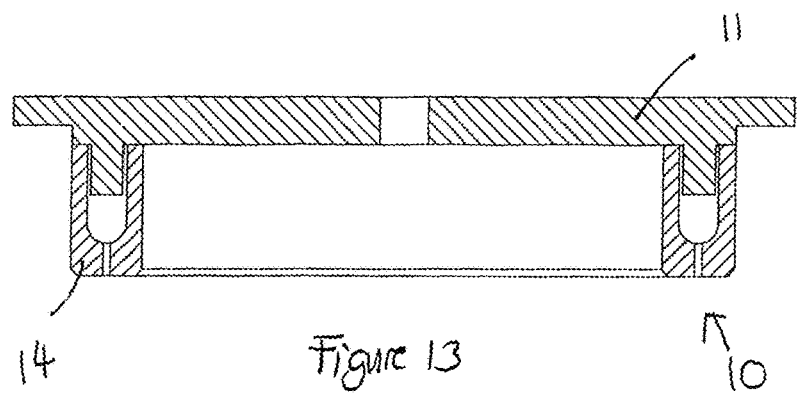
FIG. 13 illustrates a side cross-sectional view of the assembled enclosure device.
Figure 14:
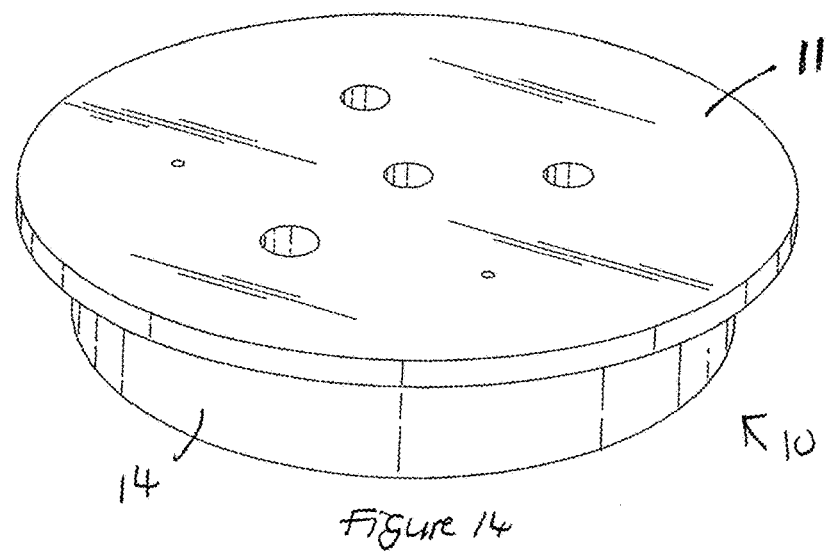
FIG. 14 illustrates a top perspective view of the assembled enclosure device.
Figure 15:
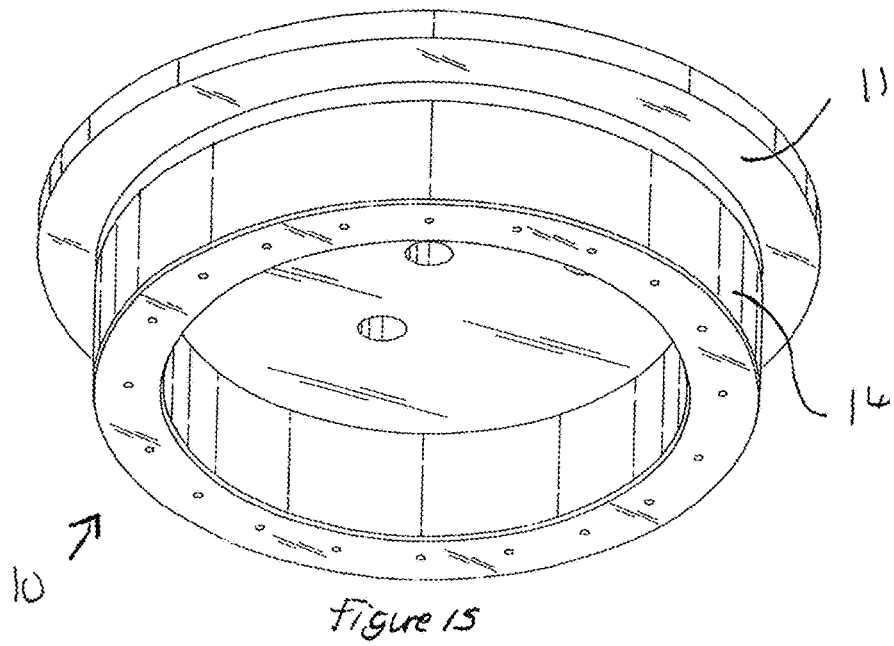
FIG. 15 illustrates a bottom perspective view of the assembled enclosure device.

FIGS. 1 to 15 illustrate an embodiment of the lid portion 11 and ring-shaped chamber 14 of enclosure device 10 of the present invention. The enclosure device 10 comprises a lid portion 11 which is attached to a ring-shaped chamber 14 which is completely or partially hollow inside 16. The lid portion 11 comprises a base plate 12 a spigot 13 and lip 15, the spigot 13 is configured to fit into the ring shaped chamber 14 and the lip 15 is configured to connect to the ring shaped chamber. In the alternative illustrated the lid portion and ring-shaped chamber are formed as separated components which are connected together, however, in the alternative they may be formed as a single component, which will obviate the need for the spigot 13 and lip 15 as illustrated in relation to the embodiment shown in FIGS. 16 to 18 discussed below. The base plate 12 has two apertures 18 that extend through the entire thickness of the base plate and through the entire thickness of the spigot 13. Each aperture 18 is configured to be connected to a supply of gas at one end thereof, this is achieved by connecting a tube 50 ideally made of metal (e.g. stainless steel or copper) into each of the apertures. The diameter of each of the apertures illustrated is 2.38 mm. Each of the tubes 50 is connected to a supply gas via a tube 52 typically formed from a plastics material which, when dissolved into the bicarbonate solution, will increase or decrease the pH. In an alternative where a single aperture is provided a t-junction may be provided which splits so that both the increasing and decreasing pH gas can be introduced using the same single aperture. The other end of the apertures 18 connect either directly or through a channel into the hollow cavity 16 in the ring-shaped chamber 14. At the bottom of the ring-shaped chamber (opposite to the base plate), a plurality of orifices 20 are made through the entire depth thereof. The distance between each of the orifices in the embodiment illustrated is about 13 mm. The diameter of each of the orifices in the embodiment illustrated is 1 mm. The angle at which each of the orifices passes through the bottom of the ring-shaped chamber is in the range of 45-90° in reference to the surface of the liquid (dissolution media) in the dissolution compartment. The orifices can be unidirectional (such as all in 90° angle in reference to the surface of the liquid) or in multiple-directions with mixed angles from 45-90° in reference to the surface of the liquid. In the embodiment illustrated the orifices are all at 90°.

In one alternative of the invention (not illustrated), the chamber is attached to the base plate and the chamber is completely hollow inside. The gas is supplied through the aperture on the base plate directly into the hollowed cavity in the chamber. In another aspect of the invention (illustrated), the chamber is attached to the base plate and the chamber is partially hollow 16 inside. The gas is supplied through the apertures 18 on the base plate through a channel into the hollowed cavity 16 in the chamber.

The material of the base plate and the chamber is acrylic glass or any other inert and non-reactive material as known in the art.

The specific dimensions of the enclosure device 10 will depend on the type and size of the compartment or vessel that holds the bicarbonate solution. This means that the dimensions of the enclosure device 10 need to match that of the compartment or vessel 54. Such a compartment or vessel can be adapted from that are used in apparatus according to United States Pharmacopeia (USP) for dissolution testing of dosage forms, namely USP-I (rotating basket), USP-II (paddle), USP-III (reciprocating cylinder) and USP-IV (flow-through) apparatus. In addition to the apertures 18 on the base plate that are used for supplying the gas, other openings/gaps/holes 22, 24, 26 can be made in the plate. These include for example, an opening in the centre of the plate 22 for passing through the paddle/basket holder 58 according to the USP apparatus, an opening/hole 24 for inserting the pH electrode 60 into the dissolution medium, and openings 26 for taking/returning test samples from the bicarbonate solution via sample tubes 56.

Figure 16:
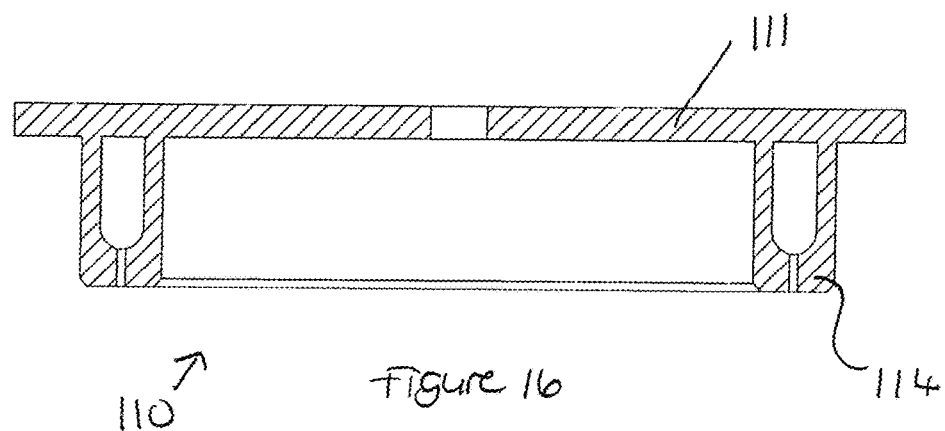
FIG. 16 illustrates a side cross-sectional view of the enclosure device formed as a single unit.
Figure 17:
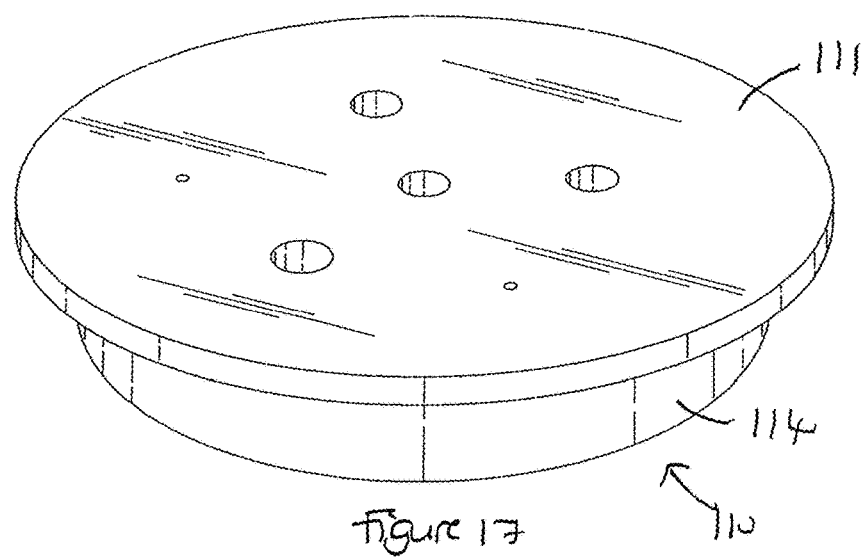
FIG. 17 illustrates a top perspective view of the enclosure device formed as a single unit.
Figure 18:
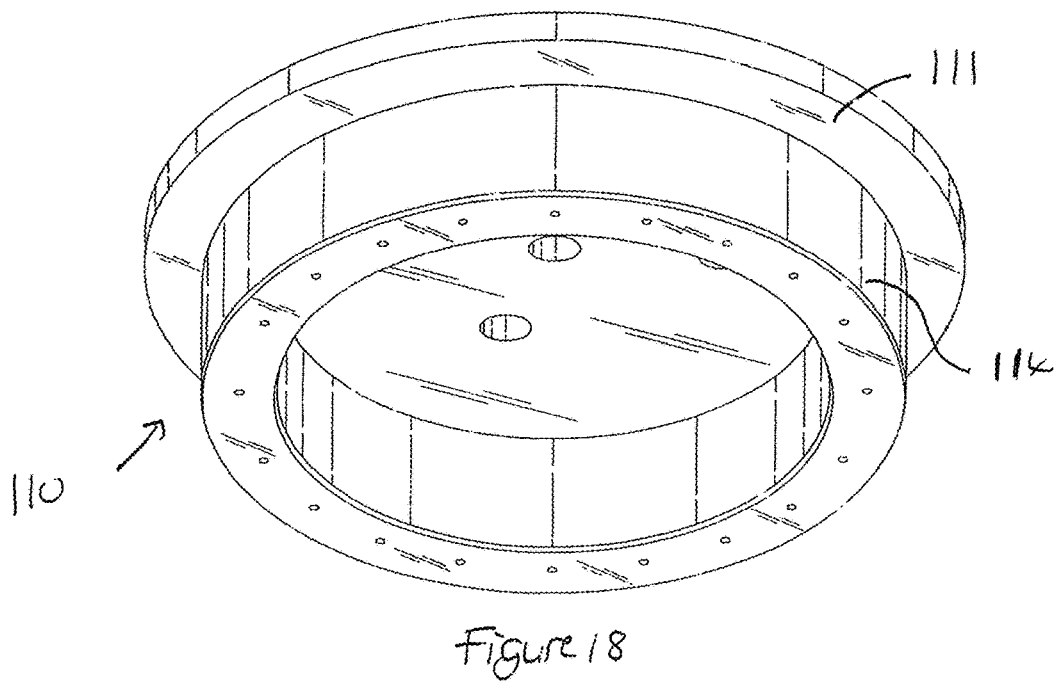
FIG. 18 illustrates a bottom perspective view of the enclosure device formed as a single unit.
Figure 19:
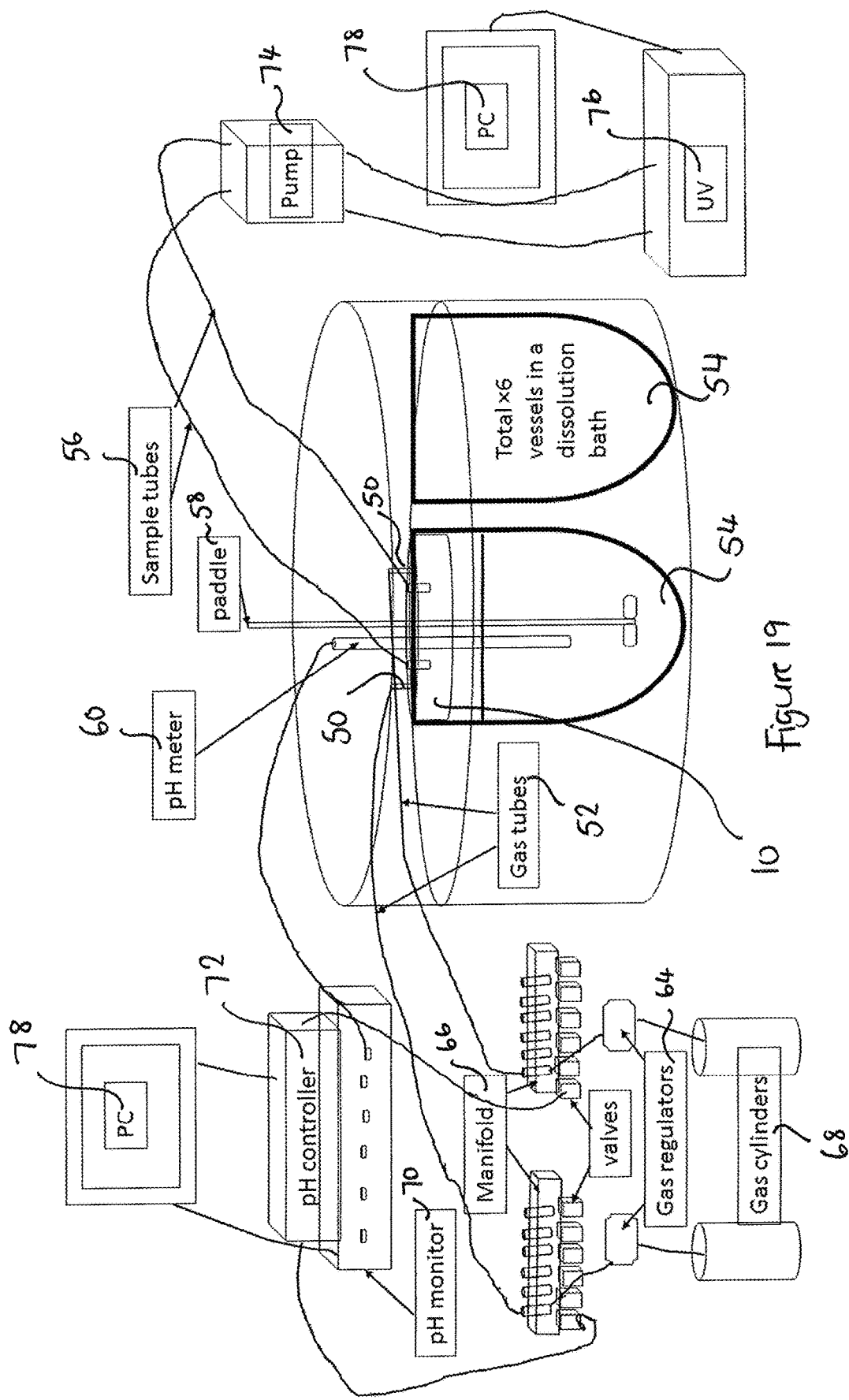
FIG. 19 illustrates a schematic of an exemplary set up of the full apparatus.

FIGS. 16 to 18 illustrate an alternate embodiment of the present invention wherein the lid portion 111 and ring-shaped chamber 114 of enclosure device 110 are formed integrally rather than as separate components. FIG. 19 illustrates a schematic of an exemplary set up of the full apparatus. The full apparatus for which the enclosure device 10 of the present invention will be used includes a dissolution bath 62, in which a plurality of vessels 54 are located. Each vessel 54 that is in use is provided with an enclosure device 10 of the present invention (also called a vessel lid). Gas tubes 52 are connected to electric valves 66, which are in turn connected to gas regulators 64 which are in turn connected to gas cylinders 68. The pH meter 60 is connected to a pH monitor 70 to monitor the pH, which in turn is connected to a pH controller 72 such that when the pH monitor detects an increase or decrease in pH as required it will communicate the same to the pH controller, which in turn will communicate to the electric valves, which in turn will communicate with the gas regulators to introduce the required gas into the system. Sample tubes 56 are connected via a pump 74 to in this case a UV spectroscopy device 76 for analysing the contents of the vessel 54 and the whole apparatus can be controlled by PC 78. In one alternative the whole apparatus is controlled by a single PC 78, in an alternative the apparatus is controlled by two PCs 78, one controlling the pH and one controlling the dissolution, as illustrated.

Example 1: Method of Preparing Bicarbonate Buffer

Hydrochloric acid aqueous solution (0.1 M, Solution A) was heated to 37° C. in dissolution vessels used for USP I and II apparatus (Table 1). Sodium hydroxide aqueous solution (2M, Solution B) was added to solution A under stirring. Ions that comprise Hanks buffer were dissolved in water to desired concentrations (Solution C). One example of such composition is NaCl (73.3 mM/L), KCl (5.370 mM/L), Mg $SO_4 \cdot 7H_2O$ (0.812 mM/L), $CaCl_2$ (1.260 mM/L), $Na_2HPO_4 \cdot 2H_2O$ (0.337 mM/L) and $KH_2PO_4$ (0.441 mM/L). Solution C and D were added to the mixture of Solution A and B under stirring and adequate volume of deionised water was added to the vessel to make the final volume to 900 ml. The pH and buffer capacity of the resultant solution was measured using the InoLab pH720 meter after 1 minute of mixing at 50 rpm with the paddle apparatus (USP II).

TABLE 1

Components for preparing bicarbonate buffer

| Solution A 0.1M HCl (ml) | Solution B 2.0M NaOH (ml) | Solution C Combination of ions (ml) | Solution D 0.2M NaHCO3 (ml) | Water (ml) | pH of buffer | Buffer capacity (mMol/L/ΔpH) |
|---|---|---|---|---|---|---|
| 700 | 34 | 100 | 24 | qs 900 | 5.6 | 1.7 |
| 700 | 34 | 100 | 32 | qs 900 | 6.0 | 4.2 |
| 700 | 34 | 100 | 41 | qs 900 | 6.2 | 7.1 |
| 700 | 34 | 100 | 63 | qs 900 | 6.5 | 8.5 |
| 700 | 34 | 100 | 78 | qs 900 | 6.8 | 10.9 |

Example 2: Method of Preparing Bicarbonate Buffer

Hydrochloric acid aqueous solution (0.1 M, Solution A) was heated to 37° C. in dissolution vessels used for USP I and II apparatus (Table 2). Sodium hydroxide aqueous solution (2M, Solution B) was added to solution A under stirring. Sodium bicarbonate powder was dissolved in Solution C (as described in Example 1) and the resultant solution was immediately added to the mixture of Solutions A and B. The pH of the resultant solution was measured using the InoLab pH720 meter after 1 minute of mixing at 50 rpm with the paddle apparatus (USP II).

TABLE 2

Components for preparing bicarbonate buffer

| Solution A 0.1M HCl (ml) | Solution B 2.0M NaOH (ml) | Solution C Combination of ions (ml) | Solution D NaHCO3 as powder (g) | Water (ml) | pH of buffer | Buffer capacity (mMol/L/ΔpH) |
|---|---|---|---|---|---|---|
| 700 | 33.2 | 100 | 0.54 | qs 900 | 5.6 | — |
| 700 | 33.8 | 100 | 0.54 | qs 900 | 6.0 | — |
| 700 | 34 | 100 | 0.54 | qs 900 | 6.2 | 4.2 |
| 700 | 34.5 | 100 | 0.54 | qs 900 | 6.5 | 4.9 |
| 700 | 34.9 | 100 | 0.54 | qs 900 | 6.8 | 3.8 |

Example 3: Method of Preparing Bicarbonate Buffer

Hydrochloric acid aqueous solution (0.1 M, Solution A) was heated to 37° C. in dissolution vessels used for USP I and II apparatus (Table 3). Sodium hydroxide aqueous solution (2M, Solution B) was added to solution A under stirring. The FaSSIF/FeSSIF powder (for Solution E) (Biorelevant.com) was dissolved in Solution C (as described in Example 1). Sodium bicarbonate powder was dissolved in the above mixture of Solutions C and E. The resultant solution was immediately added to the mixture of Solutions A and B. The pH of the resultant solution was measured using the InoLab pH720 meter after 1 minute of mixing at 50 rpm with the paddle apparatus (USP II).

TABLE 3

Components for preparing bicarbonate buffer

| Fasted or Fed status to be simulated | Solution A 0.1 M HCl (ml) | Solution B 2.0 M NaOH (ml) | Solution C Combination of ions (ml) | Solution D NaHCO3 in powder (g) | Solution E FaSSIF/ FeSSIF powder (g) | Water (ml) | Target pH of buffer |
|---|---|---|---|---|---|---|---|
| Fed | 700 | 34 | 100 | 0.54 | 11.2 | qs 900 | 5.6 |
| Fasted | 700 | 33.2 | 100 | 0.54 | 2.24 | qs 900 | 5.7 |

Example 4: pH Stabilisation at pH 6.8

Figure 20:
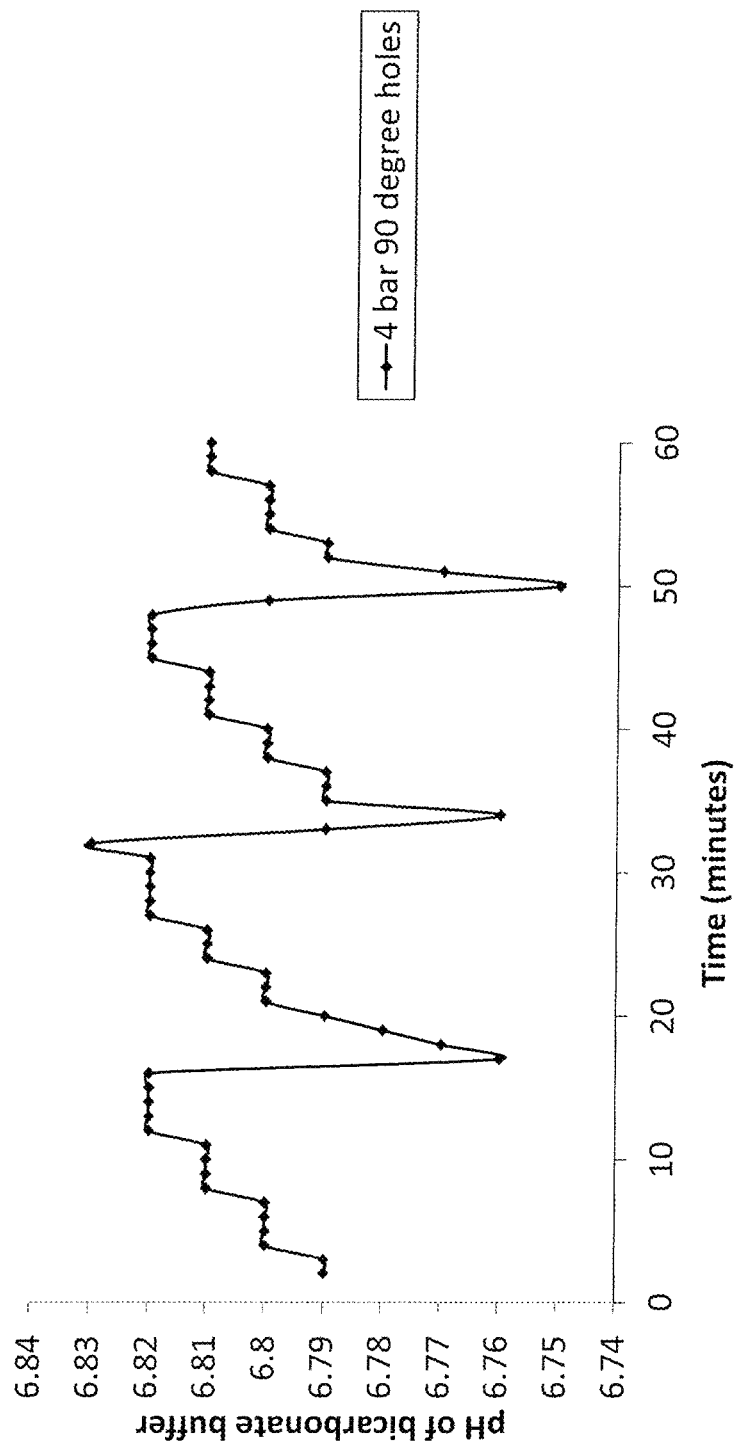
FIG. 20 illustrates a graph illustrating maintaining pH 6.8 of bicarbonate buffer.

Bicarbonate buffer of pH 6.8 was prepared using the method described in Example 2. The buffer was contained in dissolution vessels suitable for USP I and II. The vessel is enclosed using an enclosure device shown in FIGS. 1 to 15. Nitrogen (at a pressure of 4 bar (400 kpa)) and carbon dioxide (at a pressure of 0.1 bar (10 kpa)) was supplied to the vessel through the enclosure device. A Nico 2000® ELIT 6-channel pH control and monitoring system was connected to a 2-way solenoid valve to control the supply of the gases and to stabilise the pH of the solution at 6.8. FIG. 20 shows the pH changes of the solution within 60 minutes.

Example 5: pH Increase

Figure 21:
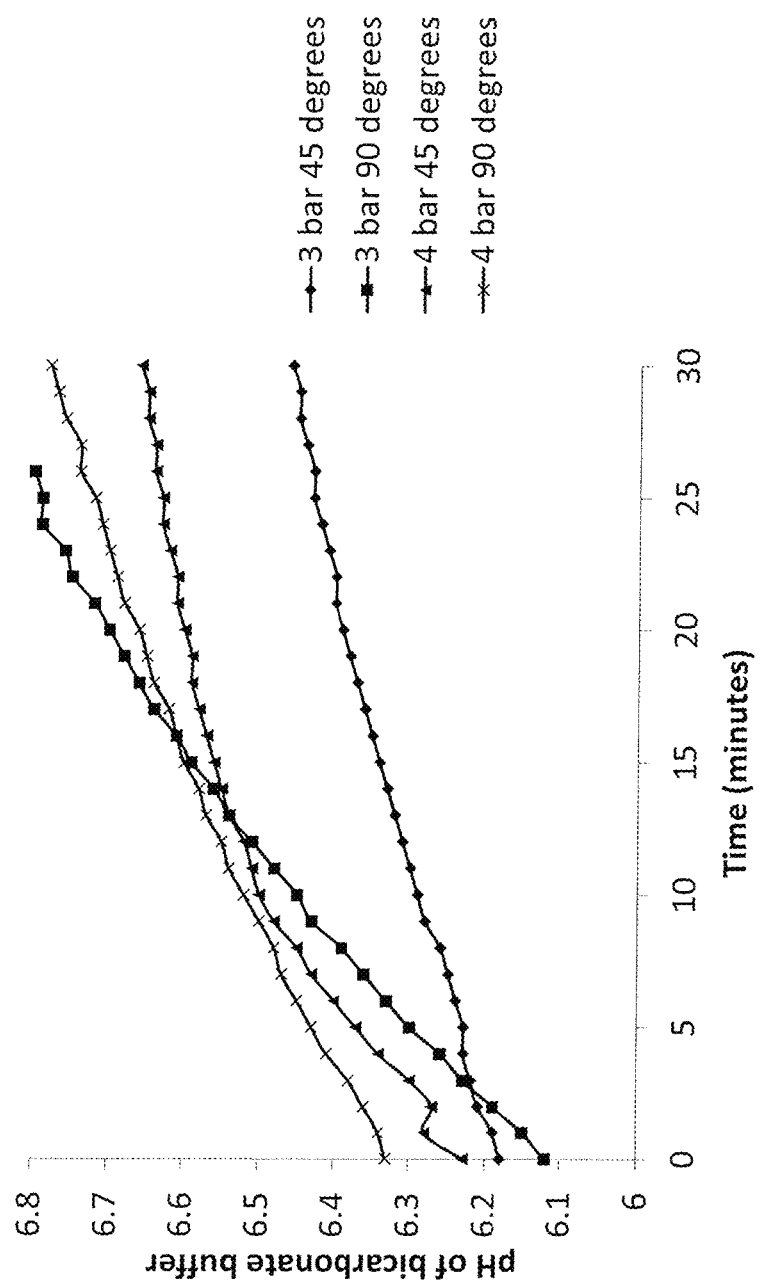
FIG. 21 illustrates a graph illustrating pH increase of bicarbonate buffer.

Bicarbonate buffer solutions of pH 6.0-6.4 were prepared using the method described in Example 2. The buffers were contained in dissolution vessels suitable for USP I and II. The vessel is enclosed using an enclosure device shown in FIGS. 1 to 15 with holes either 45 or 90 degrees in reference to the surface of the solution. Nitrogen (at a pressure of 3 or 4 bar (300 or 400 kpa)) was supplied to the vessel through the enclosure device. FIG. 21 shows the pH increase of the solution within 30 minutes.

Example 6: pH Decrease

Figure 22:
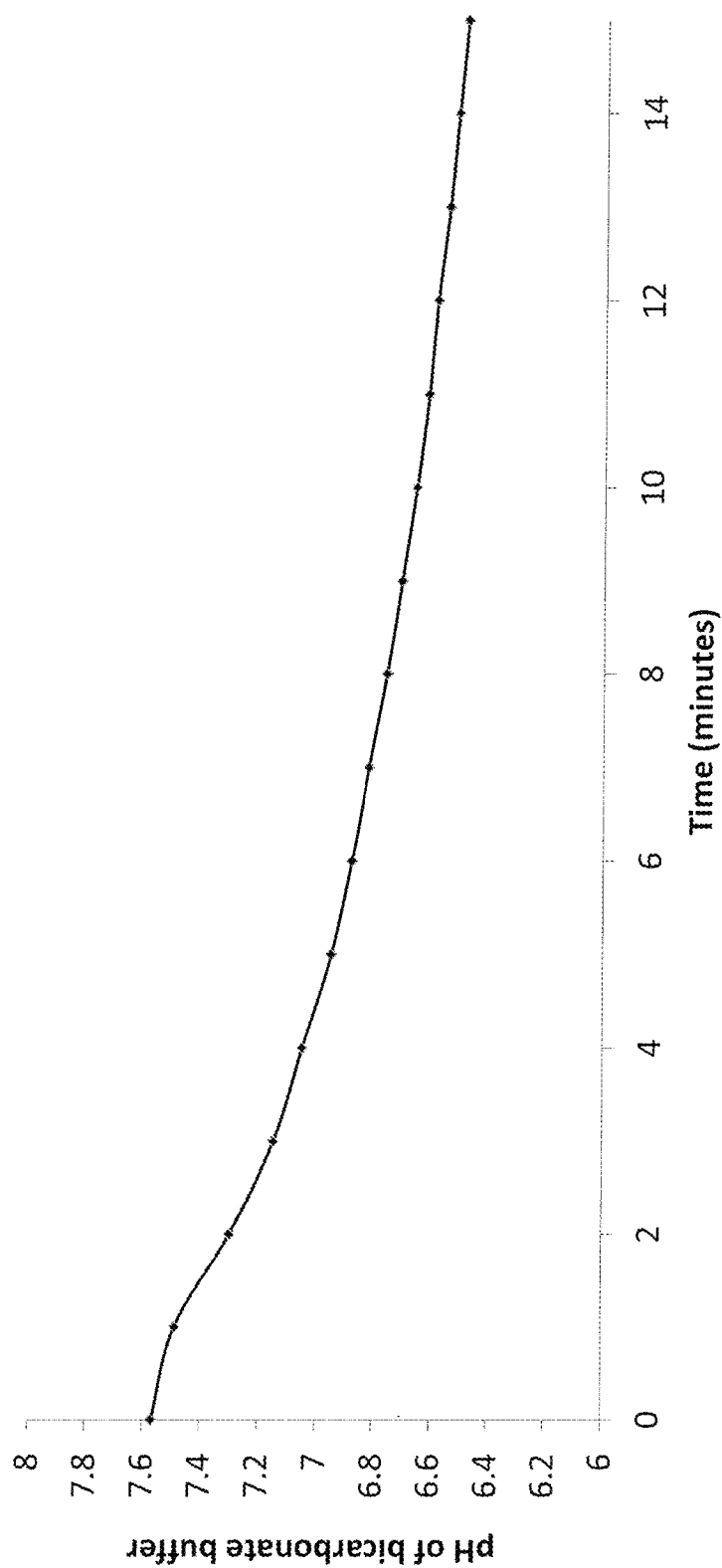
FIG. 22 illustrates a graph illustrating pH decrease of bicarbonate buffer.

Bicarbonate buffer solutions of pH 7.5 were prepared using the method described in Example 2. The buffers were contained in dissolution vessels suitable for USP I and II. The vessel is enclosed using an enclosure device shown in FIGS. 1 to 15 with holes of 90 degrees in reference to the surface of the solution. Carbon dioxide (at a pressure of 0.1 bar (10 kpa)) was supplied to the vessel through the enclosure device. FIG. 22 shows the pH decrease of the solution within 15 minutes.

Example 7: Compatibility with Bio-Relevant Media

Bicarbonate buffer of pH 6.8 was prepared using the method described in Example 3, containing FeSSIF powder simulating the fed status. The buffer was contained in dissolution vessels suitable for USP I and II. The pH of the buffer was maintained at 6.8 using two methods.

Method 1: Nitrogen (at a pressure of 0.05 bar (5 kpa)) and carbon dioxide (at a pressure of 0.05 bar (5 kpa)) were purged directly into the buffer solution.

Method 2: The vessel is enclosed using an enclosure device shown in FIGS. 1 to 15. Nitrogen (at a pressure of 4 bar (400 kpa)) and carbon dioxide (at a pressure of 0.1 bar (10 kpa)) was supplied to the vessel through the enclosure device.

Results of pH Control:

Method 1: The purge of nitrogen or carbon dioxide caused bubbles in the solution. Immediately foaming was observed in the solution which spilt out the top of the dissolution vessel. The experiment could not be continued.

Method 2: No foaming or spillage was observed during the supply of the nitrogen and carbon dioxide gases. The pH of the bicarbonate solution was maintained at 6.8±0.5 for 60 minutes.

While the present invention has been illustrated by description of various embodiments and while those embodiments have been described in considerable detail, it is not the intention of Applicants to restrict or in any way limit the scope of the appended claims to such details. Additional advantages and modifications will readily appear to those skilled in the art. The invention in its broader aspects is therefore not limited to the specific details and illustrative examples shown and described. Accordingly, departures may be made from such details without departing from the spirit or scope of Applicants' invention.

The invention claimed is:

1. An enclosure device for use in the provision of pH control and stabilization to a bicarbonate based solution used in the in vitro dissolution testing of pharmaceutical products, comprising:
a plate attached to a ring-shaped chamber, the ring-shaped chamber comprising a hollow cavity, wherein the plate comprises at least one aperture that extends through an entire thickness of the plate, the at least one aperture being configured to be connected at one end thereof to at least one supply of gas and at the other end to connect into the hollow cavity of the ring-shaped chamber, and wherein a plurality of orifices extend from the hollow cavity in a direction away from the plate through the entire thickness of the ring-shaped chamber, wherein an angle at which each of the plurality of orifices passes through the ring-shaped chamber is in the range of 45-90° relative to a horizontal plane of the plate.

2. The enclosure device as claimed in claim 1, wherein the plate comprises two or more apertures that extend through the entire thickness of the plate.

3. The enclosure device as claimed in claim 1, wherein the at least one aperture is configured to be connected to a supply of gas by connecting a tube into the at least one aperture.

4. The enclosure device as claimed in claim 3, wherein a diameter of the tube is 1-10 mm.

5. The enclosure device as claimed in claim 1 through which a gas can be supplied which, when dissolved into the bicarbonate solution, will increase or decrease a pH thereof.

6. The enclosure device as claimed in claim 1, wherein a distance between each of the plurality of orifices is in a range of 1-150 mm.

7. The enclosure device as claimed in claim 1, wherein a diameter of each of the plurality of orifices is 0.1-2 mm.

8. The enclosure device as claimed in claim 1, wherein the angle at which each of the plurality of orifices passes through the ring-shaped chamber is the same.

9. The enclosure device as claimed in claim 1, wherein the angle at which each of the orifices passes through the ring-shaped chamber is different.

10. The enclosure device as claimed in claim 1, wherein the ring-shaped chamber is in a shape of a circle or an oval.

11. The enclosure device as claimed in claim 10, wherein a diameter of the circular shape or a length of a longest side of the oval shape is 50-150 mm.

12. The enclosure device as claimed in claim 10, wherein a length of a shortest side of the oval shape is 20-100 mm.

13. The enclosure device as claimed in claim 1, wherein a height of the ring-shaped chamber is 1-50 mm.

14. An apparatus for use in the provision of pH control and stabilization to a bicarbonate based solution used in the in vitro dissolution testing of pharmaceutical products, comprising:
a compartment which is configured to contain the bicarbonate solution, wherein the compartment is enclosed with an enclosure device, comprising:
a plate attached to a ring-shaped chamber, the ring-shaped chamber comprising a hollow cavity, wherein the plate comprises at least one aperture that extends through an entire thickness of the plate, the at least one aperture being configured to be connected at one end thereof to at least one supply of gas and at the other end to connect into the hollow cavity of the ring-shaped chamber, and wherein a plurality of orifices extend from the hollow cavity in a direction away from the plate through the entire thickness of the ring-shaped chamber, and wherein the enclosure device is configured to partially isolate a gas environment in the compartment with that of the surrounding atmosphere.

\* \* \* \* \*